US006738754B1

United States Patent
Norman, Jr.

(10) Patent No.: US 6,738,754 B1
(45) Date of Patent: May 18, 2004

(54) APPARATUS AND METHOD FOR DIRECTING INTERNET USERS TO HEALTH CARE INFORMATION

(75) Inventor: James G. Norman, Jr., Tampa, FL (US)

(73) Assignee: Intermap Systems, Inc., Berkeley, CA (US)

(*) Notice: Subject to any disclaimer, the term of this patent is extended or adjusted under 35 U.S.C. 154(b) by 0 days.

(21) Appl. No.: 09/425,779

(22) Filed: Oct. 22, 1999

(51) Int. Cl.[7] .............................. G06F 17/30; G06F 7/00
(52) U.S. Cl. ................................. 707/2; 707/10; 705/2; 128/920
(58) Field of Search .................... 707/1–3, 10; 705/2–4; 600/300–301; 128/920–925, 897

(56) References Cited

U.S. PATENT DOCUMENTS

| | | | | |
|---|---|---|---|---|
| 4,667,292 A | * | 5/1987 | Mohlenbrock et al. | ......... 705/2 |
| 5,319,543 A | * | 6/1994 | Wilhelm | ......... 705/3 |
| 5,915,241 A | * | 6/1999 | Giannini | ......... 705/2 |
| 5,961,332 A | * | 10/1999 | Joao | ......... 434/236 |
| 5,964,700 A | | 10/1999 | Tallman et al. | ......... 600/300 |
| 5,974,412 A | * | 10/1999 | Hazlehurst et al. | ......... 707/3 |
| 6,113,540 A | * | 9/2000 | Iliff | ......... 600/300 |
| 6,283,761 B1 | * | 9/2001 | Joao | ......... 434/236 |
| 6,292,796 B1 | * | 9/2001 | Drucker et al. | ......... 707/5 |
| 6,302,844 B1 | | 10/2001 | Walker et al. | ......... 600/300 |
| 6,381,576 B1 | | 4/2002 | Gilbert | ......... 705/2 |
| 2001/0037215 A1 | * | 11/2001 | Sparks | ......... 705/2 |
| 2001/0051943 A1 | * | 12/2001 | Drucker et al. | ......... 707/3 |
| 2002/0007285 A1 | * | 1/2002 | Rappaport | ......... 705/2 |

FOREIGN PATENT DOCUMENTS

WO  WO-99/16407 A2 *  4/1999

OTHER PUBLICATIONS

Van Camp, A.J. "Alternatives to the Defunct AMA/Net", Online, vol. 15, No. 4, pp. 99–101, Jul. 1991.*
BetterHealth, ("www.betterhealth.com"), web site as of Jan. 25, 1998.*
PR Newswire, "A.D.A.M. Software Inc. Reports Fourth Consecutive Profitable Quarter and First Profitable Year", press release May 19, 1998.*
UC Davis Health System, "UCDHS Center for Medical Informatics: ICD–9 Coding Utility", Informatics.ucdmc.ucdavis.edu, web site as of Jul. 9, 1998.*
Business Wire "Endeavor Technologies Changes Name to WebMD, Inc.", press release, Aug. 24, 1998.*

(List continued on next page.)

Primary Examiner—John Breene
Assistant Examiner—Luke S Wassum
(74) Attorney, Agent, or Firm—Thompson Coburn LLP (57) ABSTRACT

A method of directing a patient to a source of health care information. The method comprises placing on a prescription sheet an address for the Internet web site, identifying an ailment of the patient and ascertaining an ICD or CPT code associated with the ailment. A key word or an ICD or CPT code associated with the ailment is placed on the prescription sheet and the sheet is given to the patient. The patient is instructed to input the key word or ICD or CPT code into a computer communicating with an Internet web site to obtain information about the ailment. The Internet web site and computer are configured in such a manner that the input of the key word or ICD or CPT code into the computer results in retrieval via the Internet web site of information about the ailment. Further navigation of the information within the database by the patient is made specific for that particular disease at that particular stage in its course through assigning a hierarchical system of priorities based upon the makeup of the ICD and or CPT codes contained within each segment of information.

26 Claims, 5 Drawing Sheets

OTHER PUBLICATIONS

Kansas University Medical Center, "KUMC Clinical Web Server", clinweb.kumc.edu, web site as of Sep. 16, 1998.*

Modern Healthcare, "On–Line Physician's Office", vol. 28, No. 40, pp. 34+, Oct. 5, 1998.*

Ruch, P. et al., "MEDTAG: Tag–like Semantics for Medical Document Indexing", Proceedings fo the AMIA Symposium, Nov. 6–10, 1999.*

Lovis, C. et al., "Medical Dictionaries for Patient Encoding Systems: a Methodology", Artificial Intelligence in Medicine, vol. 14, No. 1–2, Sep.–Oct. 1998.*

Kansas University Medical Center, "KUMC Clinical Web Server", clinweb.kumc.edu, Sep. 16, 1998.*

UC Davis Health System, "UCDHS Center for Medical Informatics", infomatics.ucdhs.ucdavis.edu, Sep. 27, 1997.* eICD.com (EICD Main Page), downloaded from www.eicd.com/EICDMain.htm on Feb. 26, 2002.*

U.S. National Library of Medicine (Medical Subject Headings (MeSH) Fact Sheet), downloaded from www.nlm.nih.gov/pubs/factsheets/mesh.html on Feb. 26, 2002, 2 pages.*

Merck (The Merck Manual of Diagnosis and Therapy, Seventeenth Edition, Title Page), downloaded from www.merck.com/pubs/mmanual on Feb. 26, 2002, 2 pages.*

Merck (Foreword to the Print Edition), downloaded from www.merk.com/pubs/mmanual/front/foreword.htm on Feb. 26, 2002, 1 page.*

Jones, L. D. "Building the Information Infrastructure Required for Managed Care", Journal of Nursing Scholarship, vol. 29, No. 4, Winter 1997, p. 377.*

UC Davis Health System, "UCDHS Center for Medical Informatics: ICD–9 Coding Utility", informatics.ucdmc.ucdavis.edu, web site as of Jul. 9, 1998.*

Kansas University Medical Center, "KUMC Clinical Web Server", clinweb.kumc.edu, web site as of Sep. 16, 1998.*

* cited by examiner

APPARATUS AND METHOD FOR DIRECTING INTERNET USERS TO HEALTH CARE INFORMATION

BACKGROUND OF THE INVENTION

This invention relates to apparatus and methods of directing users to health care information.

Patients, after being diagnosed with ailments, often desire information about the diagnosed ailments. Health care providers convey some information about the ailments to their patients. However, for various reasons the health care providers do not convey and/or the patients do not understand or remember all information that the patients should know. For example, time constraints with patient appointments limit the time health care providers have with their patients to explain anything but the most important aspects concerning the ailments. Also, patients often fail to think of questions or concerns about their ailments until after the conclusion of their appointments with the health care providers. Even if a health care provider provides detailed information about the ailment, a patient may not remember important information or may not understand the health care provider's nomenclature.

A tremendous amount of information about diseases and other ailments is available via the Internet. A principal problem with patients finding helpful medical information on the Internet is that patients do not have sufficient background to allow them to find information which is appropriate for their disease or group of symptoms. Furthermore, even if patients can find information specific to their diseases or conditions, they usually do not have sufficient training or insight to allow them to find where they are within the courses of their diseases or conditions. All diseases and conditions are associated with a course which can run from days (acute conditions) to decades (chronic conditions). Patients currently must rely on Internet search engines, which funnel information based upon key words. These key words are typically much too generic and result in a broad listing too voluminous to pinpoint a patient's particular ailment. For example breast cancer has at least seven histologic variants which can be diagnosed by seven distinctly different biopsy methods, and at least eight types of operations are currently performed for treating breast cancer. A key word search for "breast cancer" on an Internet search engine produces a generic listing of tens of thousands of pages. Even within a specific health information web site, the search listing will simply list all pages within the site which are related to breast cancer.

SUMMARY OF THE INVENTION

Among the objects and advantages of the present invention may be noted the provision of an improved method for providing to a patient specific and relevant information about an ailment of the patient; the provision of such a method which enables a health care provider to, with minimal effort, direct a patient to information about the ailment; the provision of an improved method for providing information about an ailment to a patient via an Internet web site; the provision of such a method which employs standardized codes; the provision of such a method which employs International Classification of Diseases (ICD) codes or Current Procedural Terminology (CPT) codes; the provision of an improved Internet navigational system for providing health care information to a user; the provision of such a system employing standardized codes, such as ICD or CPT codes, to enable a user to retrieve descriptive information about an ailment.

Generally, a method of the present invention comprises using a prescription pad to facilitate providing health care information to a patient. The prescription pad has a plurality of prescription sheets. The method comprises: performing a diagnostic procedure on a patient to identify an ailment of the patient; placing on at least one of the prescription sheets of the prescription pad an address for an Internet web site, information about the ailment being accessible via the Internet web site; and giving the one prescription sheet to the patient.

Another aspect of the present invention is a method of directing a patient to a source of health care information. The method comprises: identifying an ailment of the patient; ascertaining an ICD or CPT code associated with the ailment; instructing the patient to input the ICD or CPT code into a computer communicating with an Internet web site to obtain information about the ailment, the Internet web site and computer being configured in such a manner that the input of the ICD or CPT code into the computer results in retrieval via the Internet web site of very specific information about the ailment.

Another aspect of the present invention comprises providing health care information to an Internet user. The method comprises: storing descriptive information about a plurality of ailments in a computer database; providing a retrieval system accessible by an Internet user using the Internet, the retrieval system being adapted to retrieve the stored descriptive information for an ailment of the plurality of ailments upon the user initiating a signal corresponding to the ailment; furnishing prescription pads to health care providers, each of the prescription pads including a plurality of prescription sheets, the prescription sheets having placed thereon an address for the Internet web site.

Another aspect of the present invention for providing health care information to a user comprises: storing descriptive information about a plurality of ailments in a computer database, the descriptive information about each of the plurality of ailments being associated with at least one ICD or CPT code for said each of the plurality of ailments; providing a retrieval system accessible by an Internet user using the Internet, the retrieval system being adapted to retrieve the stored descriptive information for an ailment of the plurality of ailments upon the user initiating a signal corresponding to the ICD or CPT code for the ailment.

A further aspect of the present invention comprises an Internet navigational system for providing health care information to a user. The navigational system comprises a computer database and a retrieval system. The computer database has stored therein descriptive information about a plurality of ailments. Each ailment corresponds to an ICD or CPT code. The retrieval system is accessible by an Internet user using the Internet. The retrieval system is adapted to retrieve the stored descriptive information corresponding to one of the ailments upon the user initiating a signal corresponding to the ICD or CPT code associated with such ailment.

Another aspect of the present invention is a prescription pad for facilitating the providing of health care information to a patient. The prescription pad comprises a plurality of prescription sheets. At least one of the prescription sheets includes a surface having an address for an Internet web site placed thereon. The surface further has placed thereon an ICD or CPT code associated with an ailment. The Internet web site contains information about the ailment.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
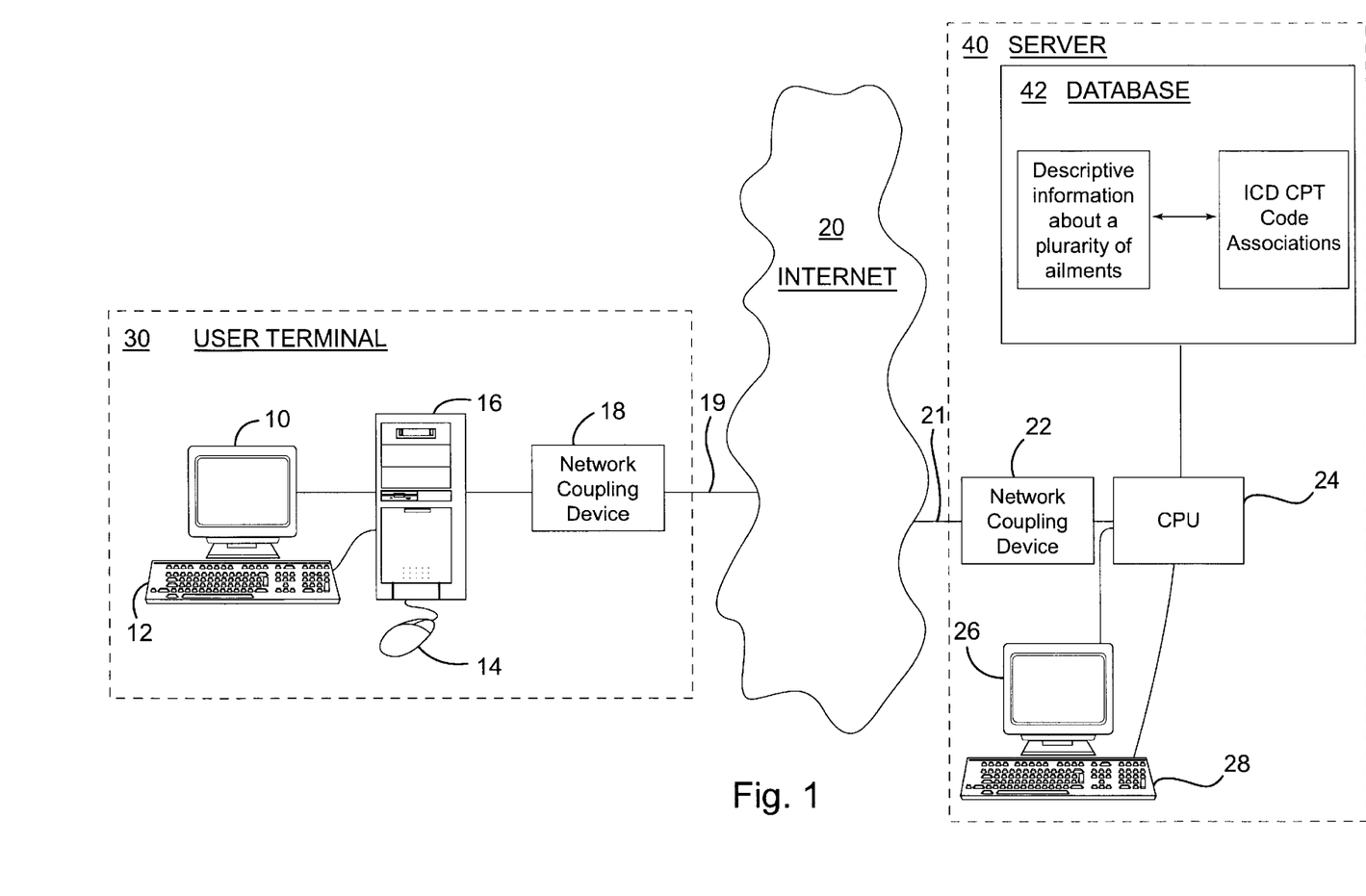
FIG. 1 is a simplified block diagram representing a computer system having an Internet navigational system of the present invention.

FIG. 1 is a simplified block diagram of a computer system in accordance with the present invention. The system comprises at least one user terminal 30 coupled to the Internet 20 (or any other suitable communication network), and a server system (or Internet navigational system) 40 also coupled to the Internet 20. In a commercially successful system, it is anticipated that there would be large numbers of user terminals of various different types in communication with the server system 40. As is conventional at present, the user terminal 30 is shown as a conventional personal computer system including a display 10, a keyboard 12, a mouse 14, a system unit 16, and a modem 18. Usually, the modem couples via a telephone line 19 to the Internet 20.

Generally, server 40 enables an Internet user to retrieve health care information, and comprises a computer database and a retrieval system. The retrieval system is preferably a database search engine (e.g., Broadvision, Verity, etc.). Server 40 is shown as a conventional computer system, rather generically comprising a network coupling device 22 of a suitable type, such as a high-speed analog or digital modem, a central processing unit (CPU) 24, and a display 26 and keyboard 28 for operator interaction. It should be understood that various means for entering data and observations other than keyboards are known. Such devices may include light pens, pointing devices such as a computer mouse, touch screens, or even microphones or video cameras or any other data input device, all of which can be configured to serve a function equivalent to a keyboard for purposes of this invention. Server 40 may, itself, be a computer network instead of the simple system shown in FIG. 1. In particular, server 40 may comprise one or more separate web servers and/or separate databases with extensive RAM and disk memory storage, or their functional equivalents. Although not shown in FIG. 1, portions of such a server network may be physically separate from one another, and these portions may communicate with each other over the Internet 20 or over a separate network. Server 40 is preferably functionally coupled to the Internet 20 and thus to terminals 30 via one or more dedicated, high-speed lines 21. The requirements for server 40 and high-speed line 21 are dictated at least in part by the expected volume of data to be exchanged with users at user terminals and by the number of such user terminals and users that are expected to access server 40.

Network 20 may usually be expected to be a public network such as the Internet, but need not be. Server 40 and its network connection are preferably selected based upon their anticipated peak loading requirements. As an example of a starting point from which to specify a server 40 and a network connection suitable for use with the invention, high-speed connection 21 could be a standard T1-type connection to the Internet provided by an Internet Service Provider (ISP). Server 40 itself could comprise dual INTEL® P3 processors. The web server software could be any that allows the server to communicate via a standard protocol. On the Internet, this would include the well-known TCP/IP and Web-based (HTTP, SHTTP) protocols. Examples of such servers are NETSCAPE® Server 3.0 and MICROSOFT® Internet Information Server (IIS). Preferably, server 40 will also comprise a hardware database server (not separately shown in FIG. 1). A person skilled in the art, upon understanding the nature of the inventive system and given the implementation details, would be able to select and configure appropriate server hardware. The database software should preferably be sufficiently fast and powerful to handle the anticipated user volume. Preferably, database software that may be useful in conjunction with the invention is produced by Oracle Software and Microsoft Corporation, and may include, for example, MS SQL Server. The software used to actually run the application interface used by the Web user to interact with the database and Web servers could include such well-known software as HTML, C, C+, C++, VRML, ColdFusion®, JAVA®, and CGI.

The computer database has stored therein descriptive information about a plurality of ailments, each corresponding to very specific ICD or CPT codes. The retrieval system is adapted to retrieve the stored descriptive information corresponding to one of the ailments upon the user initiating a signal corresponding to the ICD or CPT code associated with such ailment.

As used herein, the term "ailment" shall include diseases and/or other physiological and mental conditions, with such conditions not necessarily being limited to abnormalities.

The term "CPT codes" stands for Physician's Current Procedural Terminology codes and comprises a listing of descriptive terms and identifying codes for reporting medical services and procedures performed by physicians. The purpose of the terminology is to provide a uniform language for accurately describing medical, surgical, and diagnostic services. It provides an effective means for reliable nationwide communication among physicians, patients, and third parties. CPT descriptive terms and identifying codes currently serve a wide variety of important functions in the field of medical nomenclature. This system of terminology is the most widely accepted nomenclature for the reporting of physician procedures and services under government and private health insurance programs. CPT is also useful for administrative management purposes such as claims processing and for the development of guidelines for medical education and research by providing a useful basis for local, regional and national utilization comparisons. CPT codes are updated on an annual basis through the combined efforts of many individuals and organizations and are published through many outlets, including most medical organizations, providers, and the U.S. and most other governments. Most CPT codes are 5 digit codes, which can be modified by a number of suffixes.

As used herein, "ICD codes" means International Classification of Diseases codes. In 1948, the World Health Organization (WHO) published a statistical listing for tracking both morbidity and mortality. This listing, the International Classification of Diseases (ICD) led to the current text in international use today, the ICD ninth edition (ICD-9). This version precisely delineates the clinical picture of each patient, providing exact information beyond that needed for statistical groupings. ICD-9 codes are comprised of letters and numbers ranging from one letter and two numbers (generic diagnosis such as breast cancer) to one letter followed by 5 or more numbers. The extra digits constrict the diagnosis to become more specific.

All procedures and diagnosis within both the CPT and ICD-9 nomenclature systems can be grouped into related procedures and diagnosis by their sequence of numbers and/or letter(s). Likewise, certain ICD-9 codes can be expected to be associated with certain CPT codes with extreme frequency, while vast numbers of other CPT codes would never be associated with that particular ICD-9 code. Through knowledge of these associations and through assigning importance to the position a particular number (or letter) holds within a series of numbers (and letters) within a particular ICD-9 and/or CPT code (e.g., numbers more important than letters, first numbers more important than all other numbers within that specific code, followed by the second, third, fourth, and so on), only a small, finite number of potential associated codes are possible.

To provide for smooth, reliable and extremely accurate navigation of an extremely large database of healthcare information, each segment of information (text, video, movies, pictures, illustrations, and other health tools) is assigned appropriate ICD-9 and CPT codes. Any particular segment of information within the database may have one or multiple ICD-9 and/or CPT codes. When multiple codes are assigned, the first code of each type is given a higher priority within the navigational hierarchy, followed by the second, then the third, and so on.

By initiating a signal corresponding to an ICD-9 or CPT code associated with an ailment, a user may retrieve detailed information about the ailment from the database 22. Preferably, the ailment information stored in the database 22 comprises one or more of the following: the physiological aspects of the ailment, the pathological aspects of the ailment, information as to whether the ailment is treatable, information about expected clinical course, typical drawings, illustrations, graphs, and video, and potential complications. In other words, the Internet navigational system 20 enables users to access appropriate information as to disease stage, diagnosis, testing, symptoms, potential complications and expected clinical course.

The presence of the Internet navigational system 40 allows treating physicians or other health care providers to "prescribe" a visit to an informational web site employing the system. In particular, the health care provider advises the patient to access the web site and upon receiving a suitable prompt at the web site to input a specific ICD-9 code and/or CPT code. The use of the ICD-9 or CPT codes enables a health care provider to direct a patient to the precise information pertinent to the patient's ailment in its current state. By assigning ICD-9 and CPT codes to each portion of information within the Internet database, and assigning navigational hierarchy priorities, the patient navigating this Internet sight never has more than a few follow-up page choices at any one time.

A patient diagnosed with breast cancer may be directed to detailed information about her particular condition or treatment options by a physician instructing her to input one or more specific ICD-9 or CPT codes. Use of the coding system also allows patients (with simple instruction by their health care providers) to immediately find information about treatments options concerning their ailments, such as information about the specific type of operation they are about to have or about the specific drug prescribed for treating their disease. The physician can therefore have confidence that the information the patient is receiving is the precise information that the physician wants conveyed.

Figure 3A:
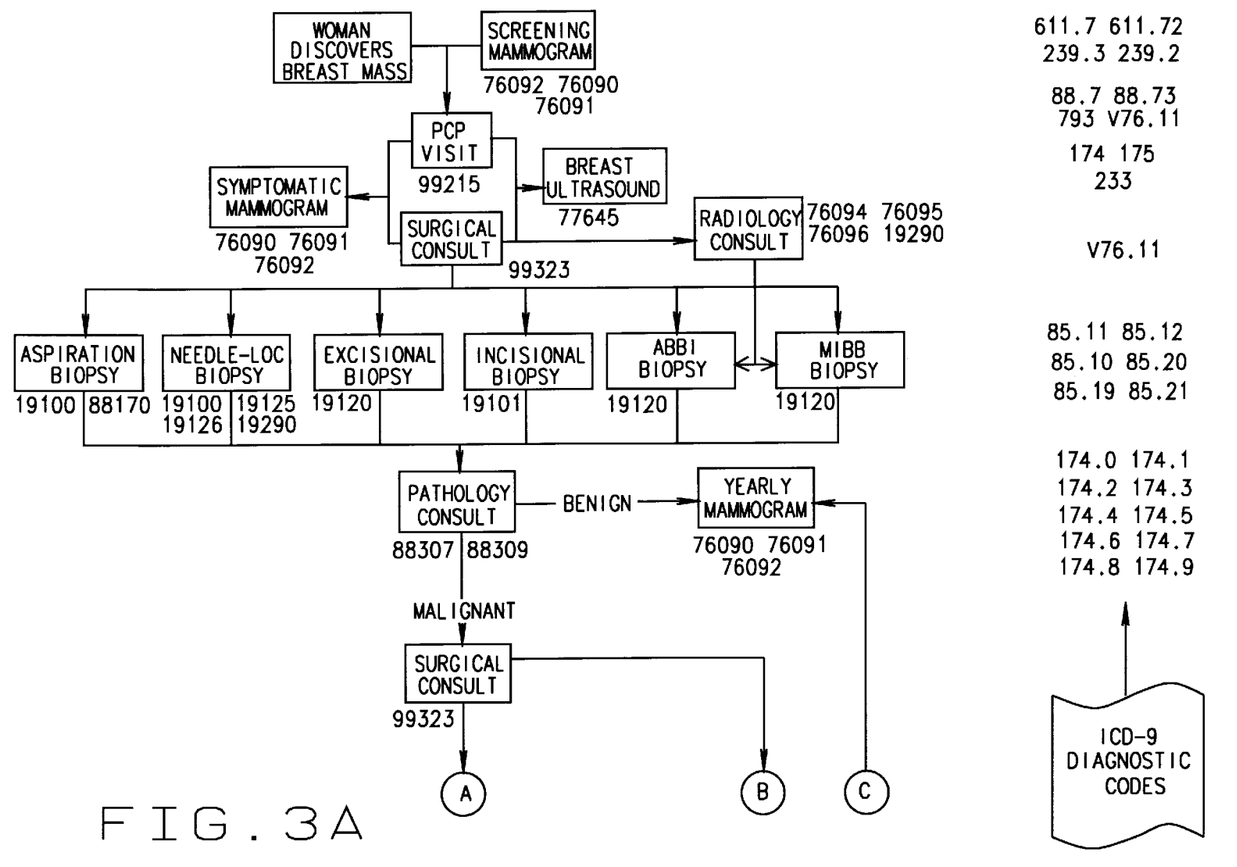
FIG. 3a is the same as a top part of the flow diagram of FIG. 2, but including ICD-9 and CPT codes for the work-up and treatment.
Figure 3B:
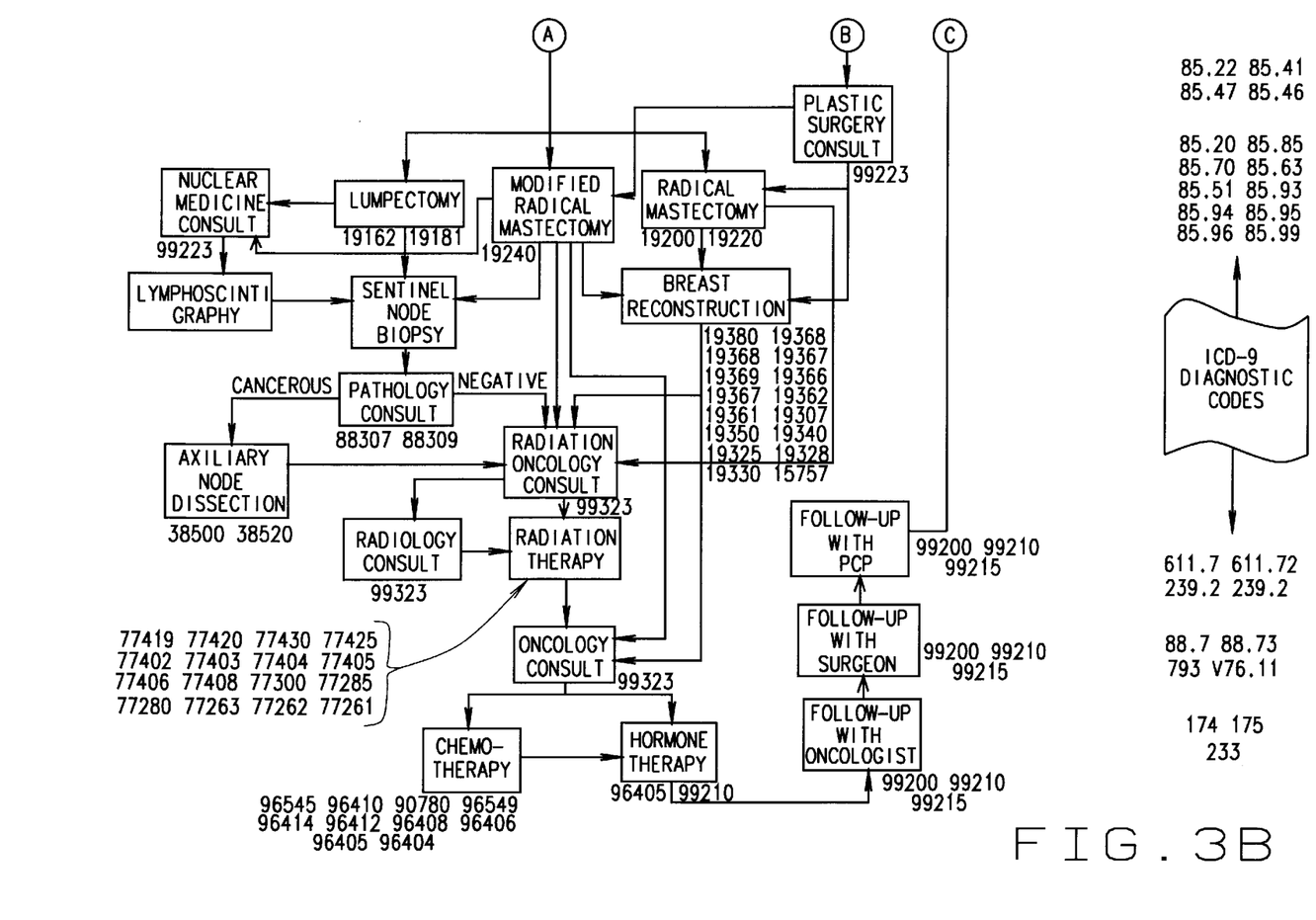
FIG. 3b is the same as a bottom part of the flow diagram of FIG. 2, but including ICD-9 and CPT codes for the work-up and treatment, FIGS. 3a and 3b combining to form the flow diagram of FIG. 2.

Once the patient has found his/her appropriate disease within the Internet site, the nature of the navigation system will allow him/her access only to appropriately related pages according to the hierarchy assigned to each page's ICD-9 and CPT codes (as illustrated for breast cancer in FIGS. 3a and 3b). Furthermore, links to other pages within the Internet site pertinent to the page being presented to the patient are displayed in the order in which they would occur in the natural history of that disease (e.g., mass discovery prior to biopsy, biopsy prior to definitive surgery, definitive surgery prior to reconstructive surgery, etc.). Thus a patient with no previous knowledge of the expected course and diagnostic and therapeutic options relating to a particular disease, can easily navigate through potentially thousands of related portions of information, accessing only those portions of information which are pertinent to their disease process, in the order in which they are likely to occur. Without this system, patients cannot adequately narrow the search to obtain the pertinent information desired. Instead, search results using prior systems or methods include information only remotely related to their condition, regardless of whether or not it will ever have clinical relevance.

Figure 2:
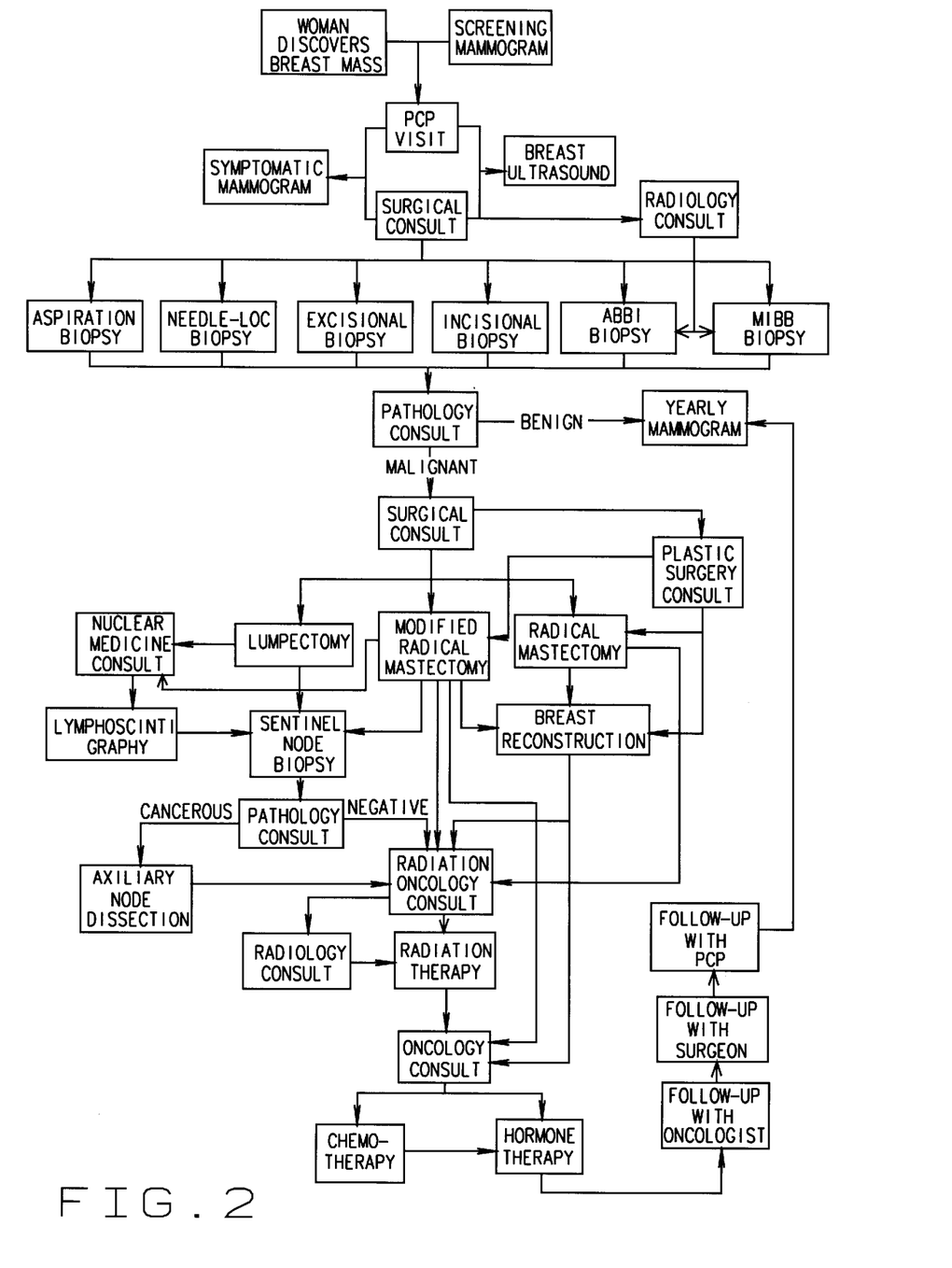
FIG. 2 is a flow diagram showing the possible paths of work-up and treatment for a patient with a breast mass.

For example, breast cancer currently encompasses fifty-three major ICD-9 and 104 major CPT codes. As shown in FIGS. 2, 3a and 3b, a patient may take any one of 7,644,119,000 different pathways during the diagnosis, treatment, and follow-up of a breast mass. In this example, a patient instructed by her physician to input a CPT code corresponding to a lumpectomy (e.g., code #19162) will input the code into a suitable prompt at the web site. By doing so, the patient will retrieve information about a lumpectomy. The patient will also be prompted by the web site to chose to retrieve information about the next level of work-up after lumpectomy (e.g., nuclear medicine consult and sentinel node biopsy). In the example of FIGS. 2, 3a and 3b, a patient navigating the Internet sight never has more than eight follow-up page choices at any one time, and typically has four or less. With this type of hierarchy, the patient can be directed to the information most pertinent to her ailment and stage of treatment.

Figure 4:
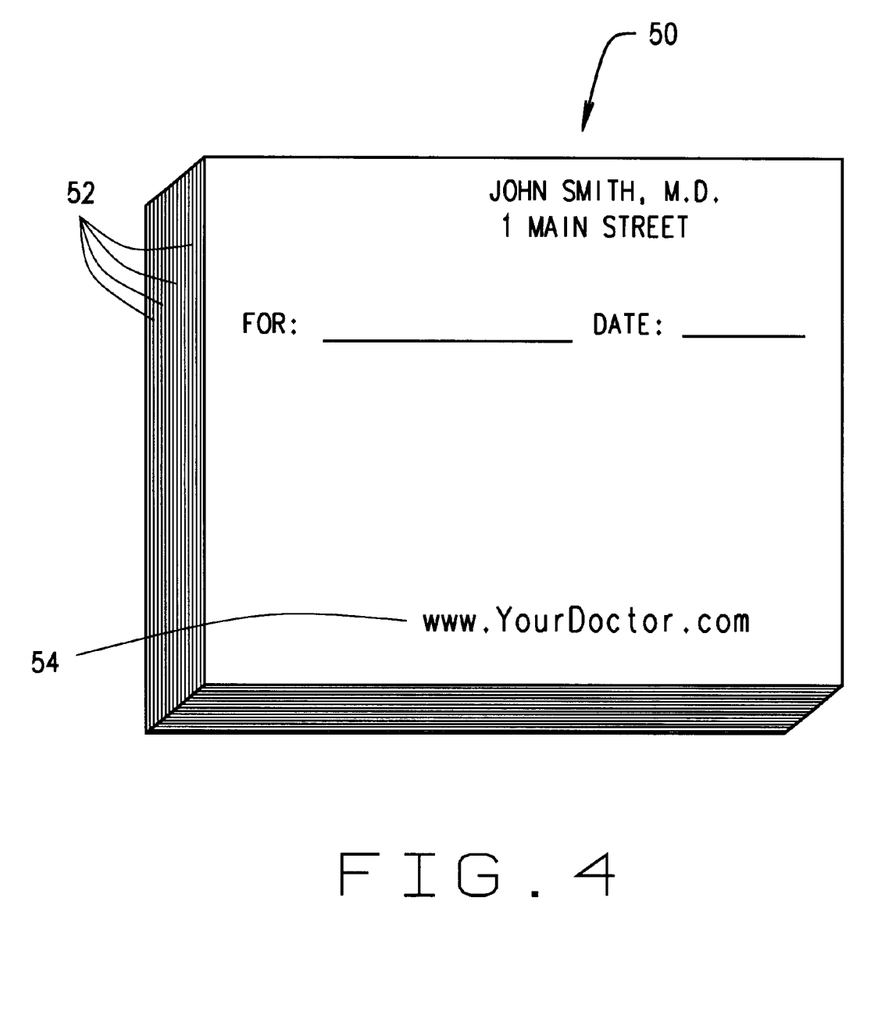
FIG. 4 is a perspective view of a prescription pad of the present invention, the prescription pad having a plurality of prescription sheets.

In FIG. 4, a prescription pad of the present invention is generally indicated at 50. The prescription pad 50 includes a plurality of prescription sheets 52. Preferably, each of the prescription sheets 52 includes an Internet web site address 54 pre-printed thereon. The sheets 52 of the prescription pad 50 may be blank other than the web site address 54. Alternatively, the sheets of the prescription pad may include additional information relevant to a particular health care provider's practice (e.g., orthopedic surgeons, family practice physicians, etc.). For example, the prescription pad may be preprinted with a listing of a plurality of ailments commonly diagnosed or treated by the health care provider.

The prescription sheets enable doctors or other health care providers to prescribe a specific part of the web site by placing on the prescription sheet key words (e.g., an operation name) or a specific ICD-9 or CPT code related to the ailment in question.

In practice, the health care provider performs a diagnostic procedure on a patient to identify an ailment of the patient.

The address for the Internet web site is placed on the prescription sheet. It may be provided to the health care provider with the Internet web site address preprinted thereon or it may be placed on the prescription sheet by the health care provider. The health care provider ascertains an ICD-9 or CPT code associated with the ailment and preferably writes the ICD-9 or CPT code on the prescription sheet. The health care provider gives the prescription sheet to the patient and instructs the patient to input the ICD-9 or CPT code into a computer communicating with an Internet web site to obtain information about the ailment. It is to be understood that the Internet web site and computer are configured in such a manner that the input of the ICD-9 or CPT code into the computer results in retrieval via the Internet web site of information about the identified ailment.

As an alternative to use of the codes, the health care provider may give the prescription sheet to the patient and instruct him/her to input a specific key word associated with the ailment into a computer communicating with the Internet web site to obtain information about the ailment. It is to be understood that the Internet web site and computer are configured in such a manner that the input of the key word into the computer results in retrieval via the Internet web site of information relevant to the identified ailment.

It is envisioned that the prescription pads will be furnished to health care providers by the owner of an Internet web site. In practice, the Internet web site owner stores descriptive information about a plurality of ailments in a computer database. The web site owner provides a retrieval system accessible by an Internet user using the Internet. Then retrieval system is adapted to retrieve the stored descriptive information for an ailment of the plurality of ailments upon the user initiating a signal corresponding to the ailment. Preferably the descriptive information about each of the plurality of ailments is associated with at least one ICD or CPT code for each of the plurality of ailments, and the retrieval system is adapted to retrieve the stored descriptive information for an ailment of the plurality of ailments upon the user initiating a signal corresponding to the ICD or CPT code for the ailment. The owner of the web site directs the health care providers to write on the prescription sheets the ICD or CPT codes associated a diagnosed ailment and then to give the prescription sheet to the patient so diagnosed.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method of providing healthcare information to a user comprising:
   storing descriptive information about a plurality of ailments in a computer database, the descriptive information comprising one or more of the following:
      physiological aspects of the ailment, pathological aspects of the ailment, information as to whether the ailment is treatable, information about expected clinical course, and information about potential complications, the descriptive information about each of the plurality of ailments being associated with a plurality of ICD or CPT codes;
   providing a retrieval system accessible by an Internet user using the Internet, the retrieval system being adapted to receive the stored descriptive information associated with one of the ICD or CPT codes upon the user initiating a signal corresponding to said one of the ICD or CPT codes.

2. A method as set forth in claim 1 further comprising prompting the Internet user to input an ICD or CPT code.

3. A method as set forth in claim 1 further comprising retrieving from the computer database the descriptive information associated with one of the ICD or CPT codes upon the Internet user initiating a signal corresponding to said one of the ICD or CPT codes.

4. A method as set forth in claim 3 wherein the step of initiating a signal corresponding to said one of the ICD or CPT codes comprises inputting th ICD or CPT codes.

5. A method as set forth in claim 4 further comprising providing the retrieved information to the Internet user via the Internet.

6. A method as set forth in claim 3 further comprising providing the retrieved information to the Internet user.

7. A method as set forth in claim 1 wherein the descriptive information comprises physiological aspects of the ailment.

8. A method as set forth in claim 1 wherein the descriptive information comprises pathological aspects of the ailment.

9. A method as set forth in claim 1 wherein the descriptive information comprises information as to whether the ailment is treatable.

10. A method as set forth in claim 1 wherein the descriptive information comprises information about expected clinical course.

11. A method as set forth in claim 1 wherein the descriptive information comprises information about potential complications.

12. An Internet navigational system for providing healthcare information to a user comprising:
   a computer database having stored therein descriptive information about a plurality of ailments, the descriptive information comprising one or more of the following:
      physiological aspects of the ailment, pathological aspects of the ailment, information as to whether the ailment is treatable, information about expected clinical course, and information about potential complications, the descriptive information about each of the plurality of ailments being associated with a plurality of ICD or CPT codes; and
   a retrieval system accessible by an Internet user using the Internet, the retrieval system being adapted to retrieve the stored descriptive information associated with one of the ICD or CPT codes upon the user initiating a signal corresponding to said one of ICD or CPT codes.

13. A method comprising:
   providing a server, the server being adapted to retrieve descriptive information about a plurality of ailments, the descriptive information comprising on or more of the following: physiological aspects of the ailment, pathological aspects of the ailment, information as to whether the ailment is treatable, information about expected clinical course, and information about potential complications, the server further being adapted to send to a user terminal communicating with the server via the Internet the descriptive information of any one of the plurality of ailments upon receiving from the user terminal a search query concerning said any one of the plurality of ailments;
   associating the descriptive information of each of the plurality of ailments with a plurality of ICD or CPT codes; and sending the descriptive information of said any one of the plurality of ailments to the user terminal via the Internet, the sending of the descriptive information being initiated by the server receiving from the user terminal the search query.

14. A method as set forth in claim 13 wherein the descriptive information comprises physiological aspects of the ailment.

15. A method as set forth in claim 13 wherein the descriptive information comprises pathological aspects of the ailment.

16. A method as set forth in claim 13 wherein the descriptive information comprises information as to whether the ailment is treatable.

17. A method as set forth in claim 13 wherein the descriptive information comprises information about expected clinical course.

18. A method as set forth in claim 13 wherein the descriptive information comprises information about potential complications.

19. A method of searching for healthcare information stored in a computer database, the healthcare information comprising a plurality of healthcare components, the healthcare components comprising a plurality of healthcare components, the healthcare components comprising one or more of the following: physiological aspects of an ailment, pathological aspects of an ailment, information as to whether the ailment is treatable, information about expected clinical course concerning an ailment, and information about potential complications concerning an ailment, the healthcare components being associated with a plurality of ICD or CPT codes, the method comprising:

accessing via the Internet a retrieval system, the retrieval system being adapted to retrieve the healthcare components associated with any one of the plurality of ICD or CPT codes upon receiving a signal, the signal corresponding to said any one of the plurality of ICD or CPT codes;

inputting the signal in a manner such that the retrieval sysytem retrieves the healthcare components associated wit said any one of the plurality of ICD or CPT codes.

20. A method as set forth in claim 19 wherein the step of inputting the signal comprises inputting said any one of the plurality of ICD or CPT codes.

21. An Internet navigation system for providing healthcare information to a user, the Internet navigation system being adapted for use with a computer database having stored therein descriptive information about a plurality of ailments, each ailment being associated with at least one ICD or CPT code, the Internet navigational system comprising:

a retrieval system accessible by an Internet user using the Internet, the retrieval sysytem being configured and adapted to retrieve the stored descriptive information corresponding to one of the ailments upon the user initiating a signal corresponding to one of the ailments upon a user initiating a signal corresponding to the at least one ICD or CPT code associated with such ailment, the descriptive information stored in the computer database comprising one or more of the following: physiological aspects of the ailment, pathological aspects of the ailment, information as to whether the ailment is treatable, information about expected clinical course, and information about potential complications.

22. A method as set forth in claim 21 wherein the descriptive information comprises physiological aspects of the ailment.

23. A method as set forth in claim 21 wherein the descriptive information comprises pathological aspects of the ailment.

24. A method as set forth in claim 21 wherein the descriptive information comprises information as to whether the ailment is treatable.

25. A method as set forth in claim 21 wherein the descriptive information comprises information about expected clinical course.

26. A method as set forth in claim 21 wherein the descriptive information comprises information about potential complications.

* * * * *

UNITED STATES PATENT AND TRADEMARK OFFICE
CERTIFICATE OF CORRECTION

PATENT NO. : 6,738,754 B1
DATED : May 18, 2004
INVENTOR(S) : Norman, Jr.

It is certified that error appears in the above-identified patent and that said Letters Patent is hereby corrected as shown below:

Column 8,
Line 1, replace "receive the stored" with -- retrieve the stored --
Line 55, replace "comprising on or more" with -- comprising one or more --

Column 9,
Lines 23-25, delete "the health-care components comprising a plurality of healthcare components,"
Line 40, replace "sysytem retrieves" with -- system retrieves --

Column 10,
Lines 4 and 5, replace "Internet navigation system" with -- Internet navigational system --
Line 13, replace "retrieval sysytem being" with -- retrieval system being --

Signed and Sealed this

Seventh Day of September, 2004

JON W. DUDAS
*Director of the United States Patent and Trademark Office*